(12) United States Patent
Cheung et al.

(10) Patent No.: US 9,694,180 B2
(45) Date of Patent: Jul. 4, 2017

(54) SHAPE ANALYSIS FOR FITTING IN A VISUAL PROSTHESIS

(75) Inventors: Dennis C. Cheung, San Gabriel, CA (US); Jessy Dorn, Los Angeles, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 0 days.

(21) Appl. No.: 13/097,516

(22) Filed: Apr. 29, 2011

(65) Prior Publication Data

US 2011/0270351 A1 Nov. 3, 2011

Related U.S. Application Data

(60) Provisional application No. 61/334,459, filed on May 13, 2010, provisional application No. 61/356,500, filed on Jun. 18, 2010, provisional application No. 61/330,109, filed on Apr. 30, 2010.

(51) Int. Cl.
*A61N 1/00* (2006.01)
*A61N 1/36* (2006.01)
*A61N 1/05* (2006.01)

(52) U.S. Cl.
CPC ........ *A61N 1/36046* (2013.01); *A61N 1/0543* (2013.01)

(58) Field of Classification Search
CPC .......................... A61N 1/0543; A61N 1/36046
USPC ...................................................... 607/53, 54
See application file for complete search history.

(56) References Cited

U.S. PATENT DOCUMENTS

| 5,109,844 A | 5/1992 | de Juan, Jr. et al. |
| 5,935,155 A | 8/1999 | Humayun et al. |
| 6,400,989 B1 | 6/2002 | Eckmiller |
| 6,458,157 B1 | 10/2002 | Suaning |
| 2004/0236389 A1* | 11/2004 | Fink et al. ..................... 607/54 |
| 2009/0287276 A1* | 11/2009 | Greenberg et al. ............. 607/54 |
| 2010/0057166 A1* | 3/2010 | Ahuja et al. .................... 607/53 |

* cited by examiner

*Primary Examiner* — Lindsey G Wehrheim
(74) *Attorney, Agent, or Firm* — Scott Dunbar

(57) ABSTRACT

A method of testing subjects' perception of complex shapes created by patterned multi-electrode direct stimulation of a retinal prosthesis is described. The complex shapes can be geometric shapes or characters such as letters of the alphabet and numbers.

5 Claims, 15 Drawing Sheets

FIG. 2

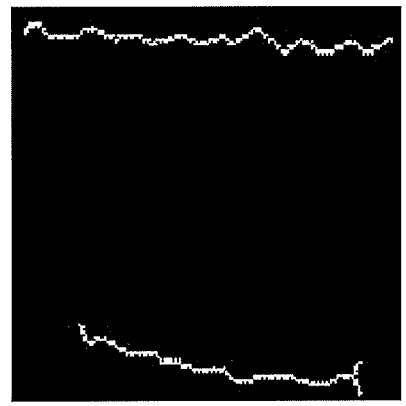
FIG. 3

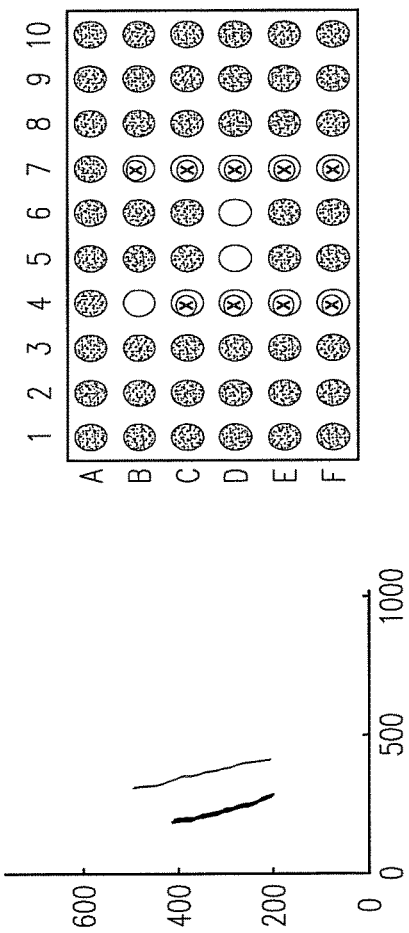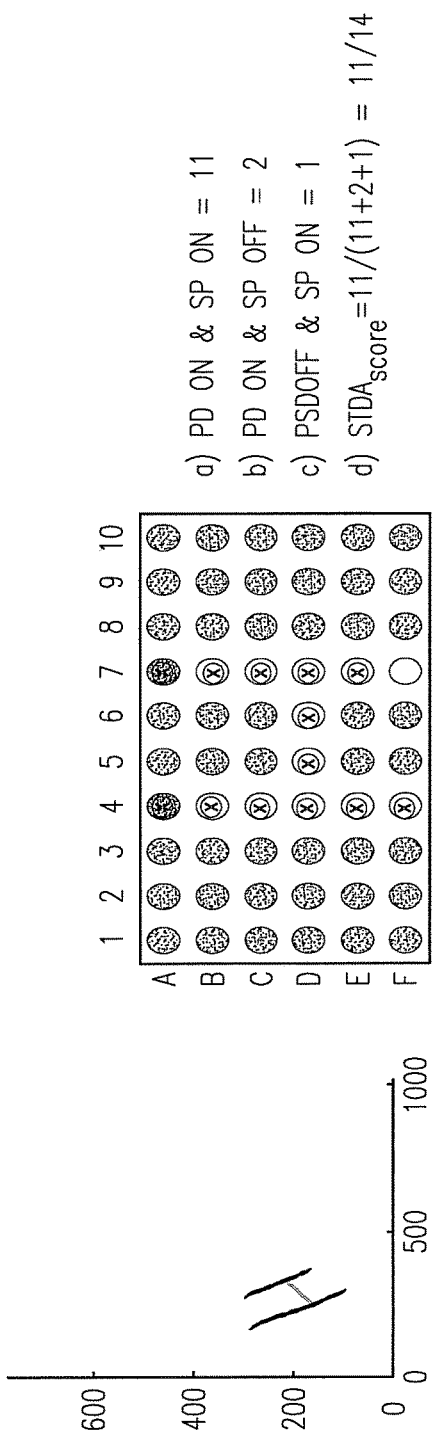
FIG. 7

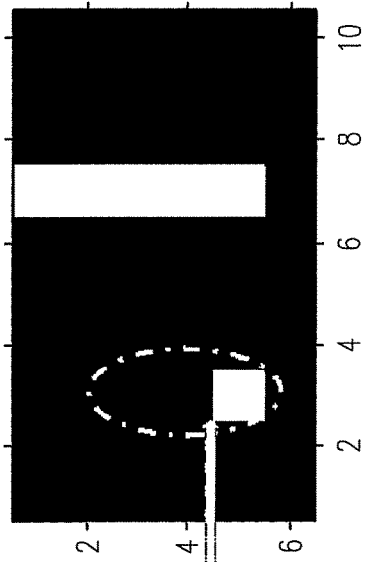
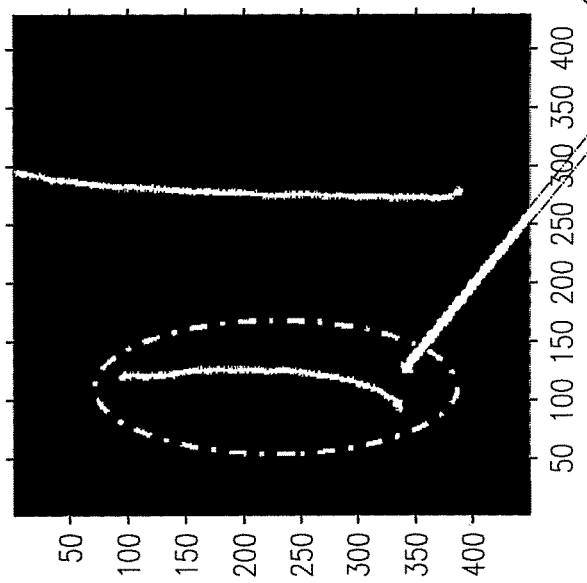
FIG. 9B
FIG. 9C
FIG. 9A

SHAPE ANALYSIS FOR FITTING IN A VISUAL PROSTHESIS

CROSS REFERENCE TO RELATED APPLICATIONS

The present application claims priority to U.S. Provisional Application No. 61/334,459 entitled "Manipulation of Frequency and Amplitude have Separable Effects on the Size and Brightness of Percepts in a Retinal Prosthesis Subject", filed on May 13, 2010, U.S. Provisional Application No. 61/356,500 entitled "Frequency Encoding of Brightness for Phosphene Size Control", filed on Jun. 18, 2010, and U.S. Provisional Application No. 61/330,109 entitled "Shape Analysis for Fitting in a Visual Prosthesis", filed on Apr. 30, 2010, the disclosures of which are incorporated herein by reference in their entirety.

The present application may be related to U.S. patent application Ser. No. 12/548,275 entitled "System and Method for Measuring and Fitting Spatio-Temporal Vision", filed on Aug. 26, 2009 and U.S. patent application Ser. No. 11/818,373 entitled "Apparatus and Method for Electrical Stimulation of Human Retina", filed on Jun. 14, 2007, the disclosures of which are incorporated herein by reference in its entirety. The present application may be further related to U.S. Pat. No. 6,920,358, granted Jul. 19, 2005, entitled "Video Processing Methods for Improving Visual Acuity and/or Perceived Image Resolution", U.S. Pat. No. 7,574,263, granted Aug. 11, 2009, entitled "Pixel Re-Mapping for Visual Prosthesis", U.S. Pat. No. 7,483,751, granted Jan. 27, 2009, entitled "Automatic Fitting for a Visual Prosthesis", and U.S. Pat. No. 7,738,962, granted Jun. 15, 2000, entitled "Fitting of Brightness in a Visual Prosthesis", the disclosures of which are incorporated herein by reference in their entirety.

The present application is also related to U.S. patent application entitled "Encoding of Size and Brightness to Percepts in Visual Prosthesis," Ser. No. 13/097,534 filed on even date herewith, the disclosure of which is incorporated herein by reference in its entirety.

STATEMENT OF GOVERNMENT GRANT

This invention was made with government support under grant No. R24EY12893-01, awarded by the National Institutes of Health. The government has certain rights in the invention.

FIELD

The present disclosure is generally directed to neural stimulation and more specifically to shape analysis for spatial fitting of a visual prosthesis.

BACKGROUND

Neural tissue can be artificially stimulated and activated by prosthetic devices that pass pulses of electrical current through electrodes on the prosthetic devices. The passage of current causes changes in electrical potentials across visual neuronal membranes, which can initiate visual neuron action potentials. These visual neuron action potentials are the means of information transfer in the nervous system.

Based on this mechanism, it is possible to input information into the nervous system by coding sensory information as a sequence of electrical pulses relayed to the nervous system via a prosthetic device. In this way, it is possible to provide artificial sensations including vision.

One typical application of neural tissue stimulation is in rehabilitation of the blind. Some forms of blindness involve selective loss of light sensitive transducers of the retina. Other retinal neurons remain viable, however, and may be activated in the manner described above by placement of a prosthetic electrode device on the inner (toward the vitreous) retinal surface (epiretinal). This placement should be mechanically stable, minimize distance between the prosthetic device electrodes and the visual neurons, control electronic field distribution and avoid undue compression of the visual neurons.

Each person's response to neural stimulation differs. In the case of retinal stimulation, even a single person's response may vary from one region of the retina to another. In general, the retina is more sensitive closer to the fovea. Also worth noting for neural stimulation is that stimulation less than a minimum threshold value would be ineffective in eliciting perception. On the other hand, stimulation beyond a maximum level would be painful and possibly dangerous to a patient. It is therefore important to map any video image to a stimulation range between a minimum and a maximum for each individual electrode. With a simple retinal prosthesis with only one or very few electrodes, it is possible to adjust the stimulation manually by stimulating and questioning the patient.

The human retina includes about four million individual photoreceptors. An effective visual prosthesis may include thousands of electrodes or more. As resolution and number of electrodes increase, it may become difficult to adjust each electrode separately by stimulating and eliciting a patient response. Therefore, a system is needed to adjust the electrodes in a visual prosthesis with multiple electrodes for size, brightness and shape of percepts without need for patient interaction in a possibly long and difficult process of characterizing each electrode individually.

SUMMARY

According to a first aspect, a method is described. The method comprising: providing a visual prosthesis adapted to be implanted in a subject, the visual prosthesis comprising an array of electrodes; selecting a first set of geometric shapes; displaying a geometric shape from the first set of geometric shapes to the subject, wherein the displaying is by stimulating electrodes in the array of electrodes corresponding to the geometric shape; describing the geometric shape perceived by the subject, thus creating a described shape; comparing the described shape to the geometric shapes from a second set of geometric shapes; and adjusting the visual prosthesis based on the comparing of the described shape, thus performing spatial fitting for the visual prosthesis.

According to a second aspect, a method is described. The method comprising: providing a visual prosthesis adapted to be implanted in a subject, the visual prosthesis comprising an array of electrodes; selecting a first set of geometric shapes; displaying a geometric shape from the first set of geometric shapes to the subject, wherein the displaying is by stimulating electrodes in the array of electrodes corresponding to the geometric shape; describing the geometric shape perceived by the subject, thus creating a described shape; comparing the described shape to the geometric shapes from a second set of geometric shapes; and adjusting the visual prosthesis based on the comparing of the described shape, thus performing spatial fitting for the visual prosthesis; and wherein the describing comprises drawing and utilizes an electronic input device and the comparing comprises utilizing optical character recognition.

According to a third aspect, a method is described. The method comprising: providing a visual prosthesis adapted to be implanted in a subject, the visual prosthesis comprising an array of electrodes; selecting a first set of geometric shapes; displaying a geometric shape from the first set of geometric shapes to the subject, wherein the displaying is by stimulating electrodes in the array of electrodes corresponding to the geometric shape; describing the geometric shape perceived by the subject, thus creating a described shape; comparing the described shape to the geometric shapes from a second set of geometric shapes; and adjusting the visual prosthesis based on the comparing of the described shape, thus performing spatial fitting for the visual prosthesis; and wherein the describing comprises drawing and utilizes an electronic input device and the comparing comprises utilizing sequence tracking detection accuracy.

According to a fourth aspect, a visual prosthesis is described. The visual prosthesis comprising: a control device adapted for selecting a first set of geometric shape; an array of electrodes configured for placement in proximity of a visual neural tissue; a neural stimulator, coupled to the control device and the array of electrodes, adapted for applying stimuli to visual neural tissue to elicit percepts and adapted for displaying a geometric shape from the first set of geometric shapes to a subject, wherein the displaying is by stimulating electrodes in the array of electrodes corresponding to the geometric shape; and means for describing the geometric shape perceived by the subject, thus creating a described shape, wherein the control device is further adapted for: comparing the described shape to the geometric shapes from a second set of geometric shapes and adjusting the selection of electrodes to be stimulated in the array of electrodes corresponding to a geometric shape from a third set of geometric shapes based on the comparing, thus improving spatial fitting for perceived image of the visual prosthesis.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 2 shows an exemplary drawn percept sample before and after a dilation morphological operation during image processing.

FIG. 3 shows an exemplary drawn percept sample before and after a thinning morphological operation during image processing.

FIG. 7 shows two exemplary calculations of sequence tracking detection accuracy (STDA) scores.

FIGS. 9A-9C show an exemplary image process involving downscaling a percept drawing to a stimulation pattern size, resulting in loss of features. FIG. 9A shows the percept drawing.

FIG. 9B shows significant loss of features after direct downscaling while FIG. 9C shows less loss of features as a result of conducting dilation morphological operation prior to downscaling.

FIG. 13 shows placement of the percept drawing in the center of the window.

DETAILED DESCRIPTION

Figure 1:
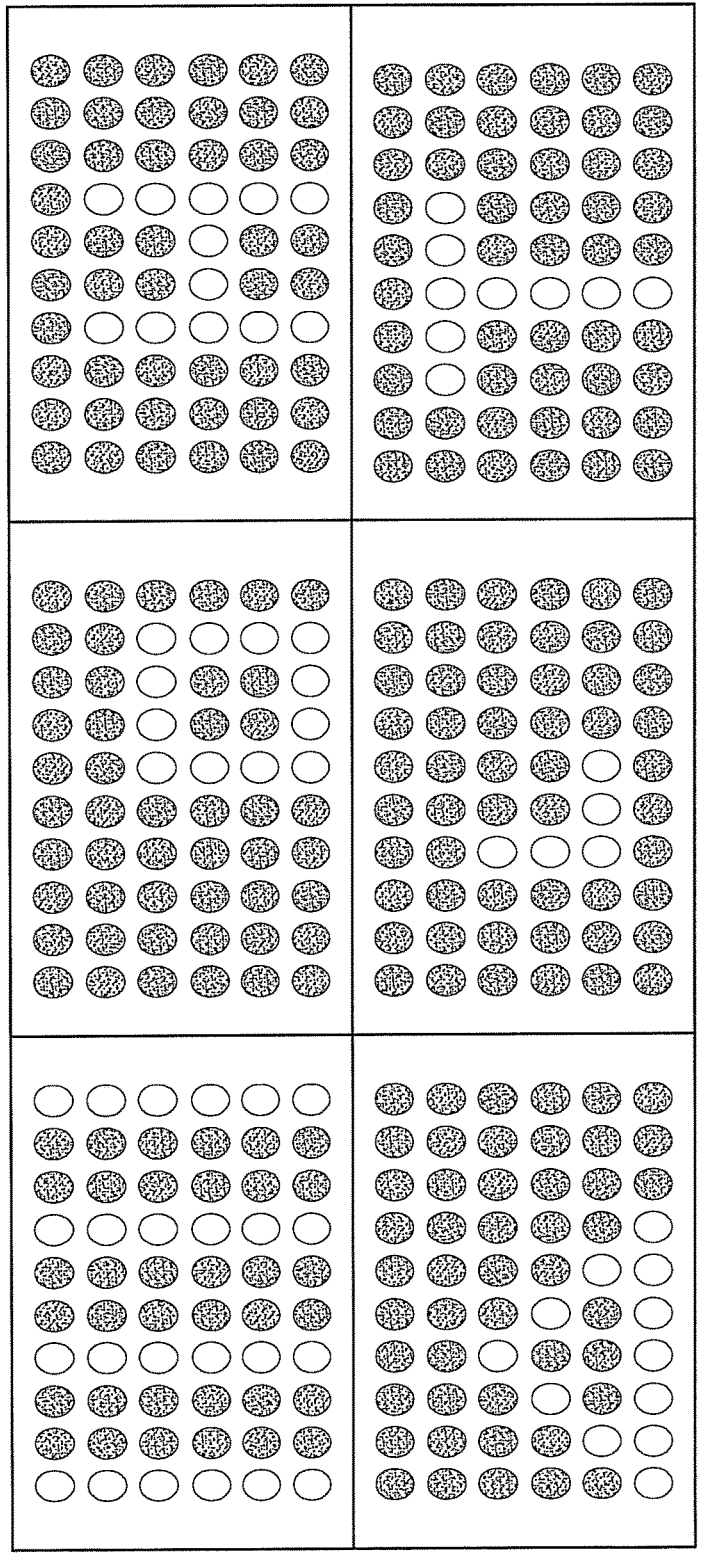
FIGS. 1A-1F show six exemplary complex shapes mapped on a 6×10 electrode array according to an embodiment of the present disclosure.

The present disclosure describes a method of testing subjects' perception of complex shapes created by patterned multi-electrode direct stimulation of a retinal prosthesis, such as the retinal stimulation system described in U.S. patent application Ser. No. 11/207,644, filed Aug. 19, 2005, entitled "Flexible Circuit Electrode Array" by Robert J. Greenberg et al., which is incorporated herein by reference in its entirety. This method of testing is referred to herein as the Complex Pattern Experiment (CPE).

Complex Pattern Experiment Overview

The present disclosure also discusses use of results of the CPE for improved spatial fitting of the retinal prosthesis. For example, the CPE can be used to test whether a subject can perceive complex shapes created by patterned multi-electrode stimulation of the retinal prosthesis. The CPE may include Optical Character Recognition (OCR) for analysis and Sequence Tracking Detection Accuracy (STDA) analysis methods for assessment of how well a percept pattern drawn by the subject matches stimulus. Thus, the CPE can give a quantitative measure of accuracy, consistency and precision for the spatial fitting.

Experimental Methods

According to an embodiment of the present disclosure, an experiment is performed on three subjects, each implanted epiretinally with a retinal prosthesis system and all of whose arrays were fully touching the retina. The array apposition is confirmed by optical coherence tomography. Each retinal prosthesis system comprises an implanted 6×10 electrode array with an electronics package which may include neuro stimulator(s) and control device(s), a video camera mounted on a pair of sunglasses adapted to record video content, and an external computer that processes the video content and determines stimulation current of each electrode in real time. Patterns of electrodes are sent directly to the epiretinal implant from the external computer (bypassing the video camera).

FIGS. 1A-1F show six exemplary complex shapes used for stimulation. The complex shape pattern can be geometric such as a triangle or represent characters, such as a number (e.g., zero) or letter (e.g., 'H'). After each stimulation, each subject is asked to draw the shape he/she perceived on a touch screen monitor.

Each complex shape pattern is formed by direct stimulation of selected electrodes of the 6×10 electrode array implant for one second each. Patterns are repeated randomly interleaved throughout all of the patterns resulting in each pattern occurring five to ten times. The selected electrodes are selected and stimulated without use of a video camera in order to determine whether subjects can perceive complex shapes without head scanning. Each experiment is repeated at two different current amplitude levels.

The results of this type of experiment can be utilized for adjustment and improvement of spatial fitting of the visual prosthesis in many ways. For example, the shape matching for a particular subject can be stored as customized settings, such as the video configuration file described in U.S. patent application Ser. No. 12/548,275 incorporated herein by reference, to serve as an automatic tool for determining stimulation input to the particular subject.

Also as an example, the adjustment and improvement of spatial fitting can be by frequency and amplitude encoding to control size and brightness of percepts as described in copending U.S. patent application entitled "Encoding of Size and Brightness to Percepts in Visual Prosthesis," filed on even date herewith.

Another more direct example can be in the case where a subject always perceives stimulation in a particular shape or class of shapes "A" as another shape or class of shapes "B", then the stimulation input to that subject can be automatically corrected when a perceived shape of "B" is desired in order to form the shape of "A" on the electrode. A range of other, perhaps more complex, models can be made for the shape transformation as part of the customized fitting for each subject's visual prosthesis.

According to an embodiment of the present disclosure, a computer is used to capture and digitize the drawn image on the touch screen monitor, but many other methods can be utilized to conduct the experiment, including different methods of capturing or describing the perceived image or shape, different methods of processing, analyzing and storing the perceived shape, and different methods of utilizing the perceived shape to conduct a spatial fit of the visual prosthesis.

Examples of capture or description methods can include asking the subject to verbally describe what the perceived shape looked like rather than the subject drawing the perceived shape on the touch screen. Alternatively, the subject can be given a limited number of choices verbally or via stimulation and be asked to make a best match.

Several examples of image processing are described in the present disclosure including morphological operations and normalizations. Some examples of analysis methods are described in the present disclosure, including optical character recognition and sequence tracking detection accuracy analysis.

Throughout this disclosure, the terms "perceived shape", "drawn shape", "drawn sample", "unknown sample", "percept drawing", "percept drawn sample", "described shape", and "test sample" are used interchangeably to describe the shape perceived and described by the subject as a result of the stimulation pattern in the electrodes by drawing or other methods. Even though the term "drawn" may be used in reference to a particular embodiment of the present disclosure, the term is meant to include non-drawing based descriptions of the percept.

Throughout this disclosure, the terms "sample" and "drawing" are used interchangeably and are defined as an image, description, or response created by a subject in response to an input image. For example, a sample can be a test sample drawn by a test subject based on a patterned electrode stimulation, or a drawing by a sighted control subject based on a image shown to the sighted control subject, or a verbal description given by a subject in response to yet another input image.

Description of the Analysis Methods

Optical Character Recognition (OCR)

A computed analysis of the complex shape pattern makes use of optical character recognition (OCR). Typical use of OCR translates scanned images of handwritten or typewritten text into machine encoded text. Similarly, in this analysis, an algorithm classifies each subject's drawing from each trial, also referred to as a test sample, to one of six classes. In this case, the six possible classes for matching to each sample correspond to the six stimulus patterns shown in FIGS. 1A-1F. The OCR algorithm in this experiment generates a classification result (closest match) based on features of the training samples and the unknown sample, but does not evaluate the quality of the match. For example, the closest match selected by the algorithm may still look quite different from the unknown sample if none of the classes are good matches.

The Applicants note that the available classes for the algorithm classification of each sample of drawn perceived patterns do not have to be the same as the set of stimulus patterns. The drawn perceived pattern may look quite different from a set of actual stimulus patterns and may be classified to a larger or different set of patterns. In the example where the subject perceives shape "A" to look like shape "B", it may be useful to include shape "B" in the set of classes for algorithm classification even if "B" is not in the set of stimulus patterns.

The steps used to build a classifier for algorithm classification can involve training and testing. In the present embodiment, 120 training samples representing each stimulation pattern is used to construct a training set of samples. Each training sample consists of a touch screen drawing by one of three (3) possible sighted control observers. Each sighted observer draws the same class for 40 times on the touch screen monitor for each of the six classes used for this experiment thus creating a total of 120 training samples for each class. For each sample, pixel data is stored and a label is assigned to the sample to identify the associated shape. The drawn samples made by the test subjects form the test set of samples. Both the training and test sets of samples can be processed utilizing the three step procedure described below.

1. Image Processing:

Throughout this disclosure, the processes of upsizing, where the number of pixels is increased proportionally, and downsizing, where the number of pixels is decreased proportionally will be discussed. The terms "upsizing" and "upscaling" will be used interchangeably to mean the same process. Similarly, the terms "downsizing" and "downscaling" will be used interchangeably.

An image of the drawn sample can be subjected to image processing. For example, the image can be normalized to a predetermined scale. In the present embodiment, a scale of 100×100 pixels is used. Normalization is beneficial for analysis because the perceived pattern drawn on the touch screen monitor by different control observers or subjects for the same complex shape can have different sizes and aspect ratios. The normalization of the image can improve robustness of a subsequent feature and reduce susceptibility to size and aspect ratio variations.

Another example of image processing is correction of rotation angle. Applicants note that the electrode array as implanted in the eye may not be perfectly aligned with the horizontal axis of the subject's head and body. Therefore, the pattern the subject perceives could be rotated at an angle. To compensate for the rotation angle and allow for common drawing skewness error, the image is also rotated ±10° from the measured array rotation on the retina at an increment of 1° to find the best match.

Morphological image processing can also be utilized in the image processing. A dilation morphological operation can be applied prior to resizing the image to 100×100 pixels. Applicants note that raw image files of drawn samples typically have a size of around 200×200 pixels or above. During the process of downsizing an image, for example from 200×200 pixels to 100×100 pixels, some structural features may be lost or eroded, especially if some lines in the pattern are thin. Dilation, which increases "thickness" of the lines in the image, can help to minimize erosion of the structural pixels. An example of image dilation is shown in FIG. 2. This type of morphological image processing helps to preserve the features of the pattern.

After downsizing, a thinning morphological operation can be applied to the image to filter out "noisy" pixels in the image, which contribute extraneous features, to retain the basic structural pixels, as shown in FIG. 3. The image after thinning morphological operation retains key pixels that are used by a classifier in feature extraction.

The terms "key pixels", "basic structural pixels", and "structural pixels" are used interchangeably thorough this disclosure and each describes key or important pixels in defining the structure or features of the image. The loss of any of such key pixels can adversely impact the quality of the analysis results for the image.

2. Feature Extraction:

Feature extraction involves parameterizing and extracting characteristics of a pattern sample so that the pattern can be stored and compared to other pattern samples of the same class or a different class. Features or parameters used for extracting the characteristics of the pattern sample can be statistical, structural or both. Examples of these features can be centroid location, skewness, kurtosis, moments, eccentricity, orientation, moment, and others. In the present embodiment, the Applicants test many features on the 720 training samples (6 classes with 120 samples per class) by plotting sets of features to look for features which are able to describe the 6 test shapes distinctively from one another.

The Applicants note that in the present embodiment, the available classes for the algorithm classification of each sample of drawn perceived patterns is chosen to be the same as the set of stimulus patterns. In other words, the training samples and the test samples are based on the same patterns although in practice they do not necessarily have to be the same.

Figure 4:
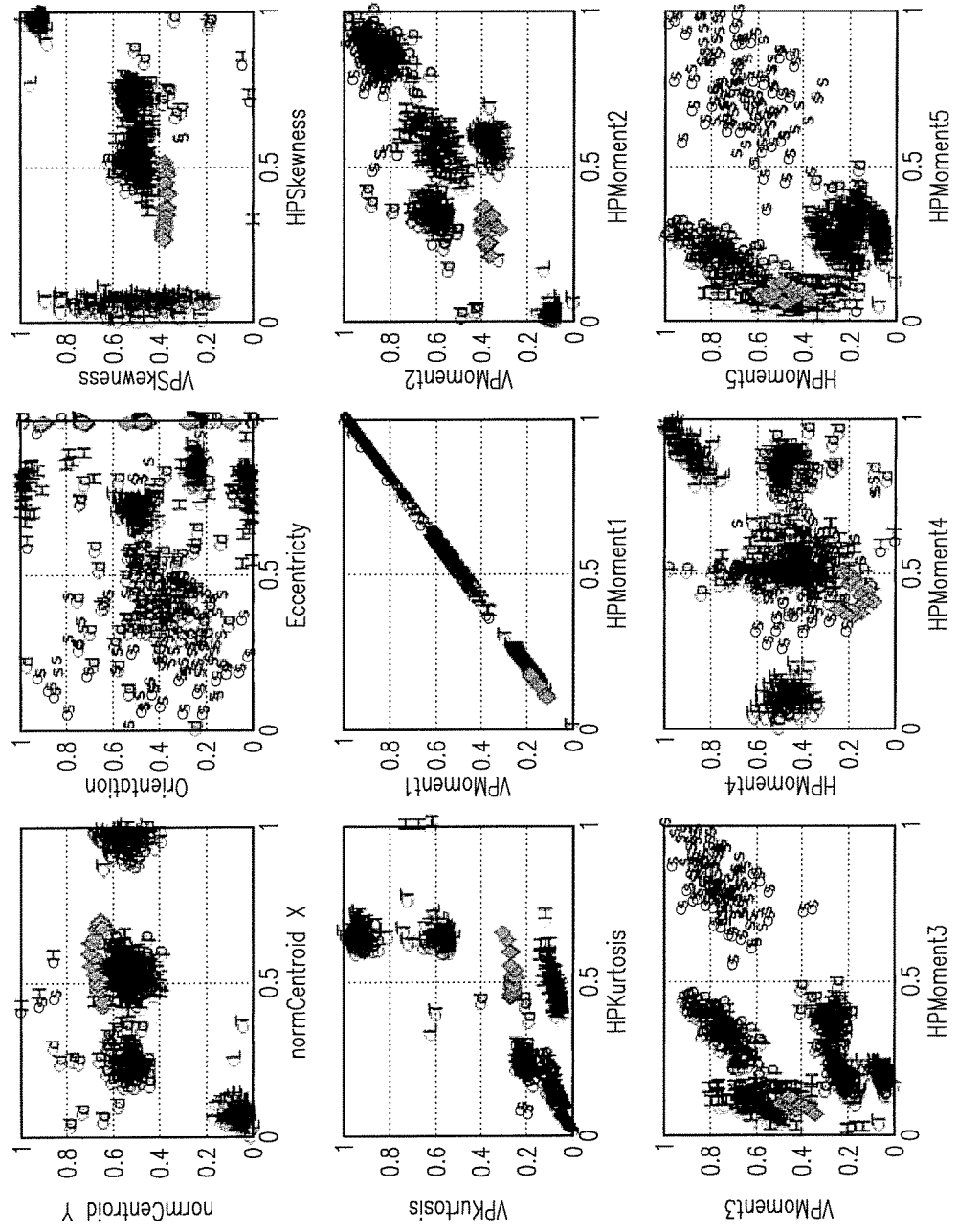
FIG. 4 shows several examples of distribution of the six (6) classes or patterns plotted on different 2-D pair-wise feature spaces.

FIG. 4 shows several examples of the distribution of different classes plotted on different 2-D pair-wise feature spaces. Possible feature choices are used to form these 2-D feature spaces with data for the 720 training samples total from the 6 available classes for the algorithm classification of each sample. Features which result in clear clusters of data for each class with distinct boundaries between each cluster of data are chosen to analyze the test samples.

For example, the top-left plot of FIG. 4 shows the feature centroid Y plotted as a function of the feature centroid X. With the exception of a few outliers, the data points for each class (shape) in the plot form a clear cluster with distinct boundaries from data points for another class on the plot. This data behavior indicates centroid Y maybe a useful feature for distinguishing each of the six classes from one another.

As another example, the top-middle plot of FIG. 4 shows orientation plotted as a function of Essentricity. The data points for each class in this plot, however, are intermixed with data points from other classes. This data behavior indicate orientation may not be useful feature for distinguishing each of the six classes from one another.

In the current embodiment, Applicants' testing by trial and error has identified seven features that give best classification performance for the six classes and are thus selected for analysis:
  i. Centroid X
  ii. Centroid Y
  iii. Eccentricity
  iv. Horizontal Skewness
  v. Vertical Skewness
  vi. Horizontal Kurtosis
  vii. Vertical Kurtosis 3. Classification:

Pattern classification can be used to aid analysis. In the present embodiment, the K-nearest neighbor (KNN) method as described in reference 1 (incorporated herein by reference in its entirety), is used to classify each test sample (the subject's drawing in a single trial) and to match each test sample to a closest stimulus class. KNN is a method for classifying unknown samples based on the K number of closest training samples plotted in a feature space.

For example, if N features are used, then the feature space would have N dimensions. Euclidean distance can be used as a distance metric in the feature space. A Euclidean matrix is computed (size of M×N where M is the number of training samples, e.g., 720 and N is the number of features, e.g. 7). The distance matrix is sorted to find the first K closest neighbors. The test sample is then classified based on a majority vote result of these K closest neighbors.

The parameter K is a set constant and the best choice for K depends on the data. In general, larger values of K are less prone to noisy data, resulting in smoother boundaries between classes as shown in reference 2 (incorporated herein by reference in its entirety). Performance of the KNN algorithm depends on both the number of selected features, N, and the parameter K indicating the number of nearest neighbors used for matching. For the present embodiment, both N and K are chosen to be 7 based on trial and error performance, but N and K can be other numbers and do not have to be the same.

Figure 5:
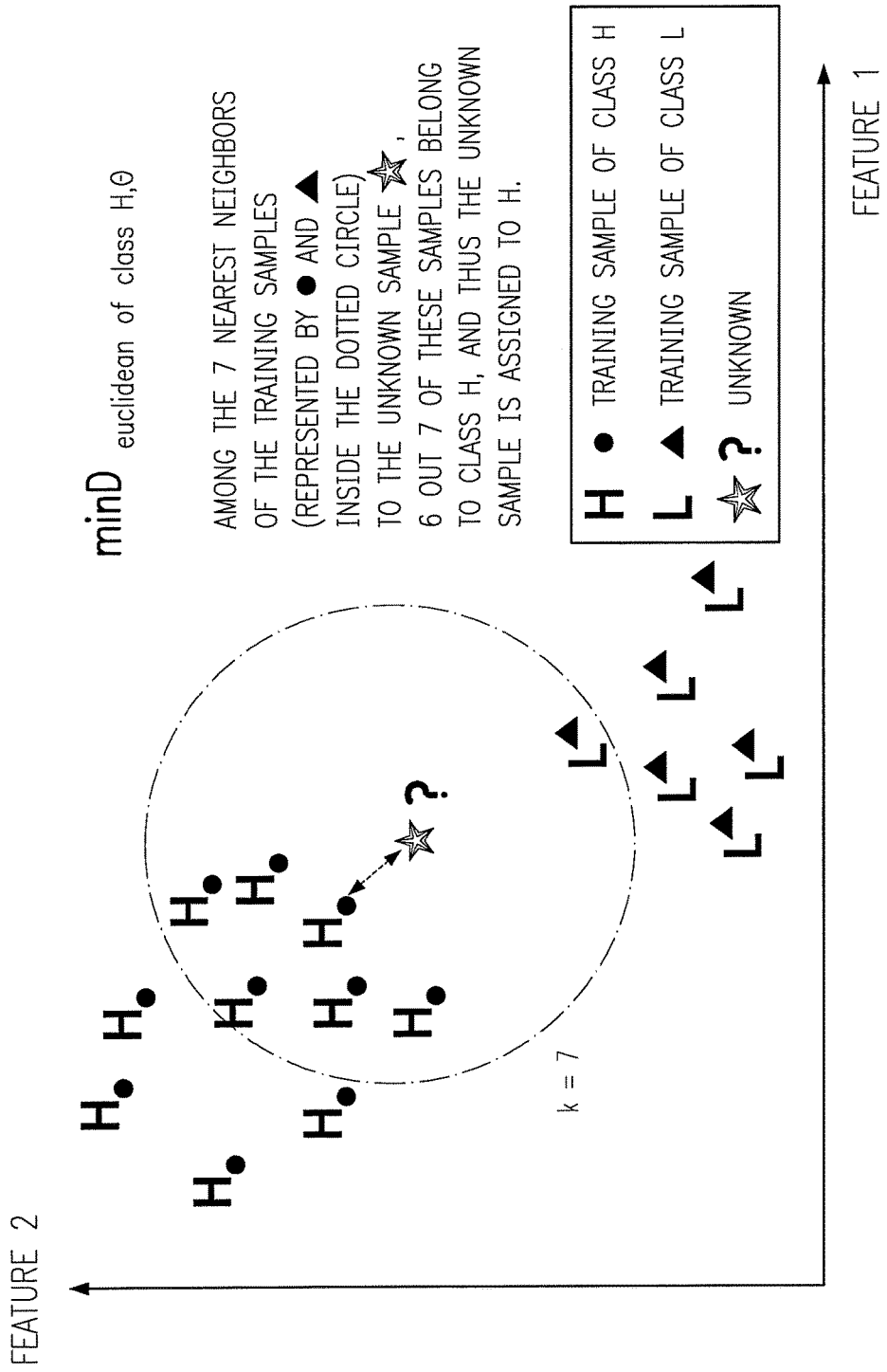
FIG. 5 shows an exemplary plot of some classes or patterns in a 2-D pair-wise feature space of Feature 1 and Feature 2, showing seven nearest matches of training samples to an unknown or a test sample.

FIG. 5 shows an exemplary plot of some training samples and a subject test sample on a 2-D (pair-wise) feature space of example features 1 and 2. The subject test sample has been subjected to image processing rotation at an angle of θ. In FIG. 5, the seven closest neighbors (represented by the dots and triangle inside the circle) to the subject test sample (represented by the star in the figure) consist of 6 'H's and 1 'L'. Since the majority of the seven closest neighbors belong to the class of 'H', the unknown sample is classified as 'H' at rotation angle θ based on a majority vote.

Figure 6:
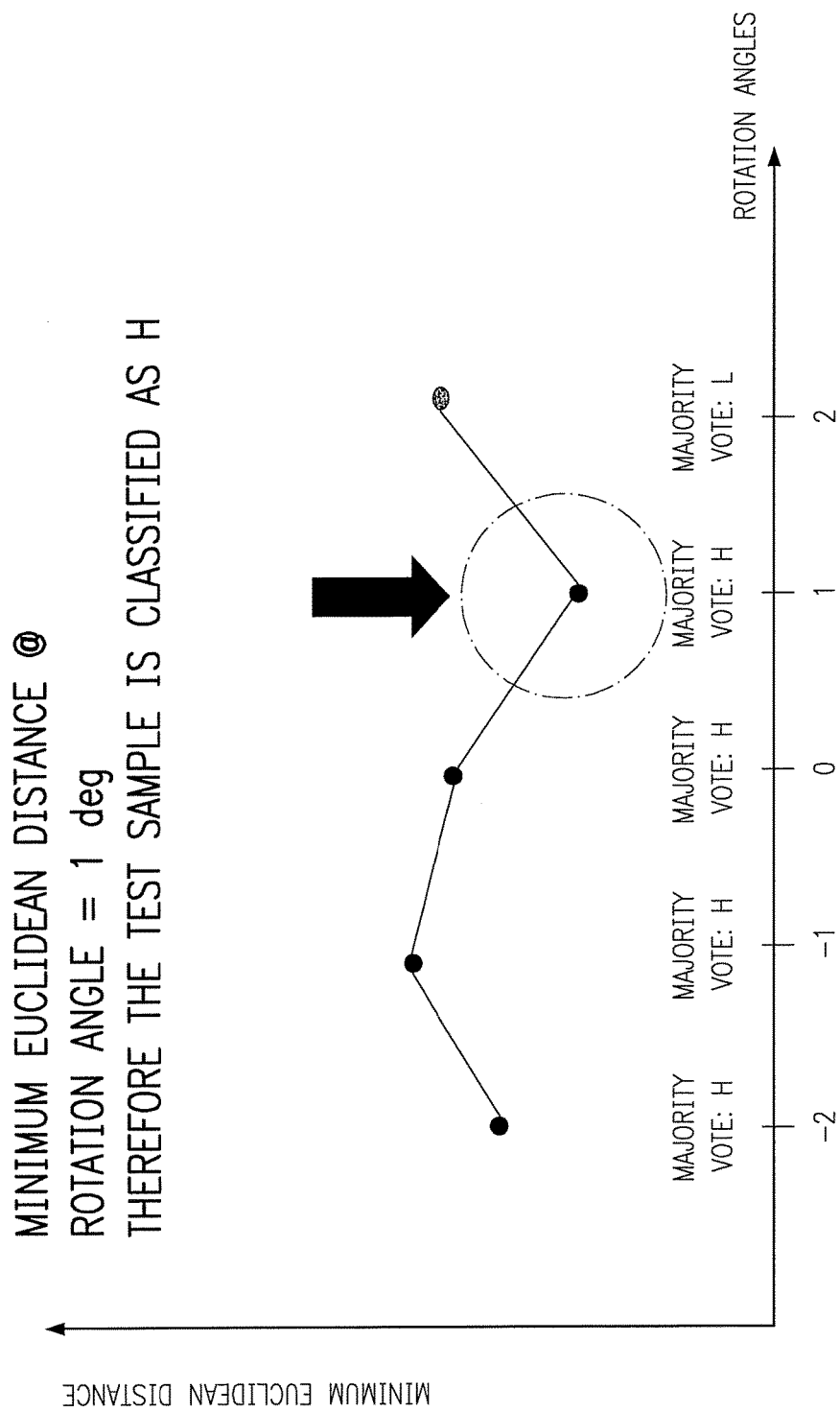
FIG. 6 shows an exemplary plot of minimum Euclidean distance of a test sample to its nearest training sample as a function of rotation angles in 1 degree increments and majority voting results.

To find a best matched class and a best matched one of rotation angle θ within the set, the same process can be repeated by rotating the test sample image ±10° from a measured array rotation on the retina, extracting the same set of features, and performing KNN classification each time. The Euclidean distance to the closest majority voted class (min $D_{euclidean\ of\ class\ H,\ \theta}$) is recorded for each rotation angle $\theta$. The class at which the minimum distance is found over the rotation angle range is the final classification for the test sample. FIG. 6 shows that the minimum Euclidean distance is found at $\theta=1°$ and that the majority of the closest neighbors belong to class 'H' for this subject test sample. Therefore, this subject test sample is classified as 'H' based on the classifier.

Sequence Tracking Detection Accuracy (STDA)

In another embodiment of the present disclosure, sequence tracking detection accuracy (STDA) as described in reference 3 (incorporated herein by reference in its entirety) is used in analysis of the drawn samples. STDA is a spatio-temporal based measure that indicates a calculated 1-to-1 match between the tracked target and a ground truth target. For the Applicants' analysis, the tracked target is the percept drawing sample (PD) and the ground truth target is the stimulation pattern (SP). The STDA score is defined as:

$$STDA_{score}=(PD \cap SP)/(PD \cup SP)$$

where PD∩SP provides the number of pixels where the pixels in the pattern coincide with the pixels in the subject drawing, and PD∪SP provides the sum of number of pixels where the pattern is present and/or where the subject drawing is present. These would include the 1) pixels in PD∩SP, 2) pixels where the pattern is present but the subject drawing does not indicate these pixels, and 3) pixels where the pattern is not present but the subject drawing indicates these pixels.

Therefore, the STDA score is a single value between 0 and 1, and it indicates how well the percept drawing matches the stimulation pattern in the realm of pixels. FIG. 7 shows two examples of calculations of the STDA score in an experiment. The top half of FIG. 7 shows an example where the shape 'H' is drawn by the subject as two parallel lines of different shape. The right side of the top half of FIG. 7 shows superposition of the 6×10 electrodes with the 'H' shape on the subject drawn sample. It shows a) nine pixels where the pattern and the subject drawing are present, b) no pixels where the subject drawing shows a feature not existing in the pattern, and c) three pixels where features in the pattern are not shown in the subject drawing and d) $STDA_{score}=9/(9+3+0)=3/4$. Similarly, the bottom half of FIG. 7 shows the STDA score of 11/14 for a second percept drawing.

The STDA calculation analysis can provide complimentary information to the OCR analysis. For example, an OCR analysis that involves knowledge of the training classes can provide a classification result, but the OCR analysis does not provide a measure of how good the match is to a class. The STDA calculation can be done without information of the training classes and provides a score showing how well the subject or training sample corresponds to the stimulation pattern.

Figure 8:
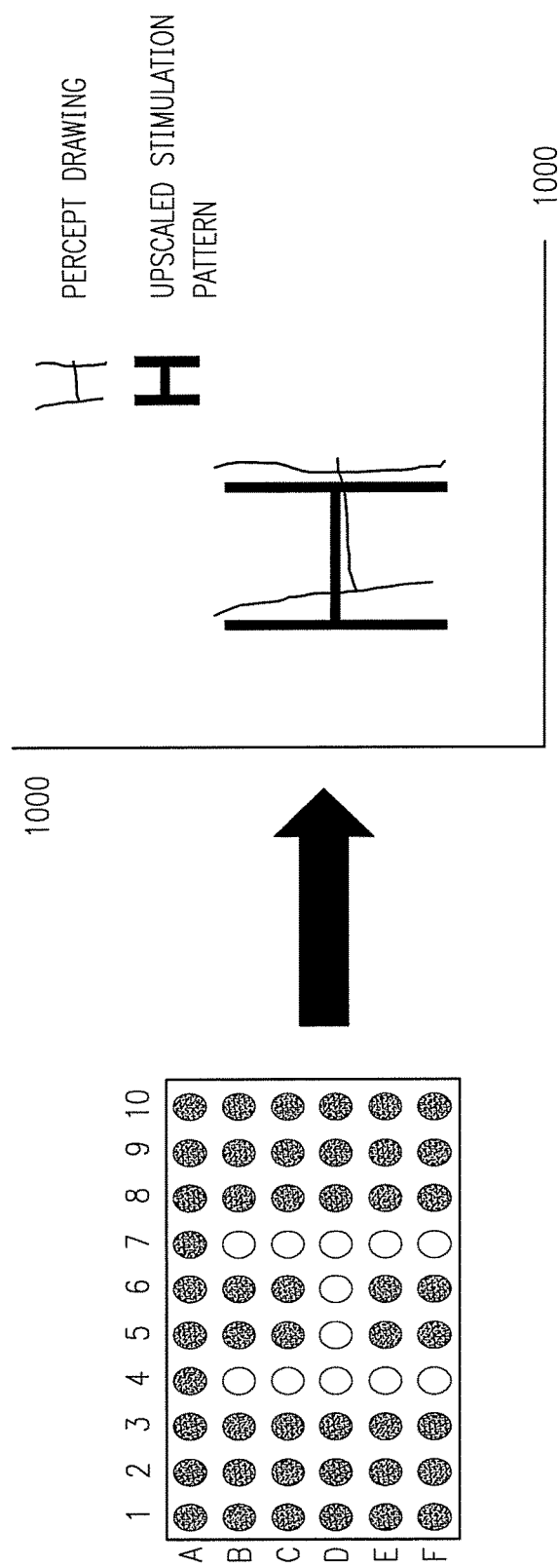
FIG. 8 shows an exemplary image process involving upscaling a stimulation pattern and projecting it to the size of a percept drawing test sample.

1. Image Processing:

As with the OCR analysis, it may be useful to conduct image processing to bring both the percept drawing and the stimulation pattern to a common pixel scale for a 1-to-1 comparison in order to find the STDA score for the percept drawing for each trial. From the example shown in FIG. 8, normalization is done to bring the percept drawing, which typically has a size of at least 200×200 pixels, to the same pixel scale as the 6×10 stimulation pattern of an embodiment of the present disclosure, for comparison. Two exemplary methods to bring the percept drawing and the stimulation pattern to the same scale are described. The two methods are 1) upscaling the stimulation pattern and projecting it to the actual perception size and 2) downscaling the percept drawing to a size equivalent to the 6×10 electrode resolution. Either process may involve morphological process of dilation and thinning as previously described in the Image processing section of the OCR analysis. In the present embodiment of the present disclosure, the first method of upscaling the stimulation pattern and projecting it to the actual perception size, as illustrated in FIG. 8, is found to produce more robust results than downscaling.

As illustrated in FIGS. 9A-9C, the Applicants observe that loss of features as indicated by structural pixels can occur if the method of normalizing is by downscaling the percept drawing to a lower resolution. FIGS. 9A-9C show a significant portion of the structural pixels is lost with a direct downscaling of the percept drawing of FIG. 9A to FIG. 9B. For the two drawn lines in the percept drawing in FIG. 9A, direct downscaling causes the entire line on the left and most of the line to the right to be lost in the downscaled drawing shown in FIG. 9B.

With morphological dilation, the feature loss from the downscaling can be reduced but not necessarily eliminated. FIG. 9C shows the result of normalizing the same percept drawing of FIG. 9A but with morphological dilation prior to downscaling to the 6×10 scale. Unlike in FIG. 9B, the drawn line on the right is preserved. However, FIG. 9C shows even with prior morphological dilation, only one-third of the drawn line on the left is preserved in the donwscaled drawing.

Based on the experimental results shown in the paragraphs above, Applicants chose upscaling as the method of to bring the percept drawing and the stimulation pattern to the same scale in spite of an advantage of faster computation time offered by downscaling as it involves less number of pixels in calculation. Normalizing by downscaling the percept drawing is shown to be a less desirable option due to probable erosion of the shape and features of the sample. This feature and shape erosion could lead to significant errors to the STDA score.

Figure 10:
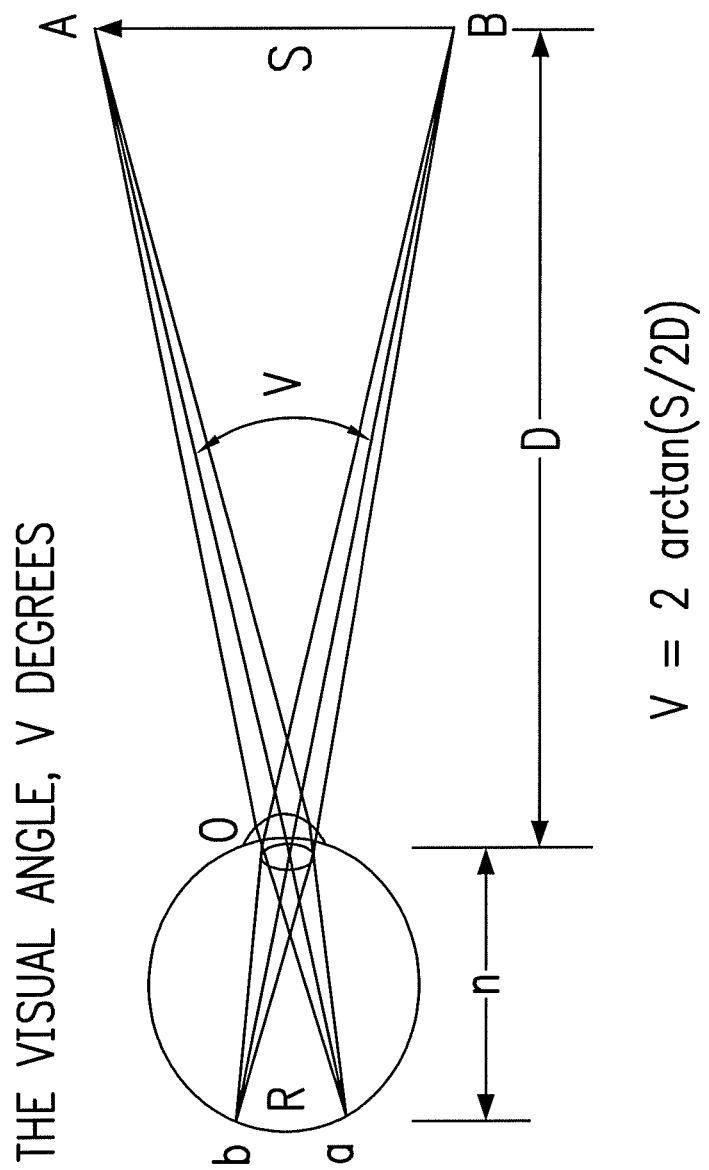
FIG. 10 shows an exemplary calculation of a visual angle, which can be used for upsizing a stimulation pattern.

With reference back to the image processing method of upscaling the stimulation pattern to the percept drawing (touch screen), the upscaling method involves a projection of the stimulation pattern. The projected stimulation pattern size can be calculated from the equation below as shown in FIG. 10 and reference 4 (incorporated by reference in its entirety):

$$V=2\ \arctan(S/2D)$$

where V=visual angle, S=projected length of the image, and D=distance between the eye and the touch screen.

Figure 11:
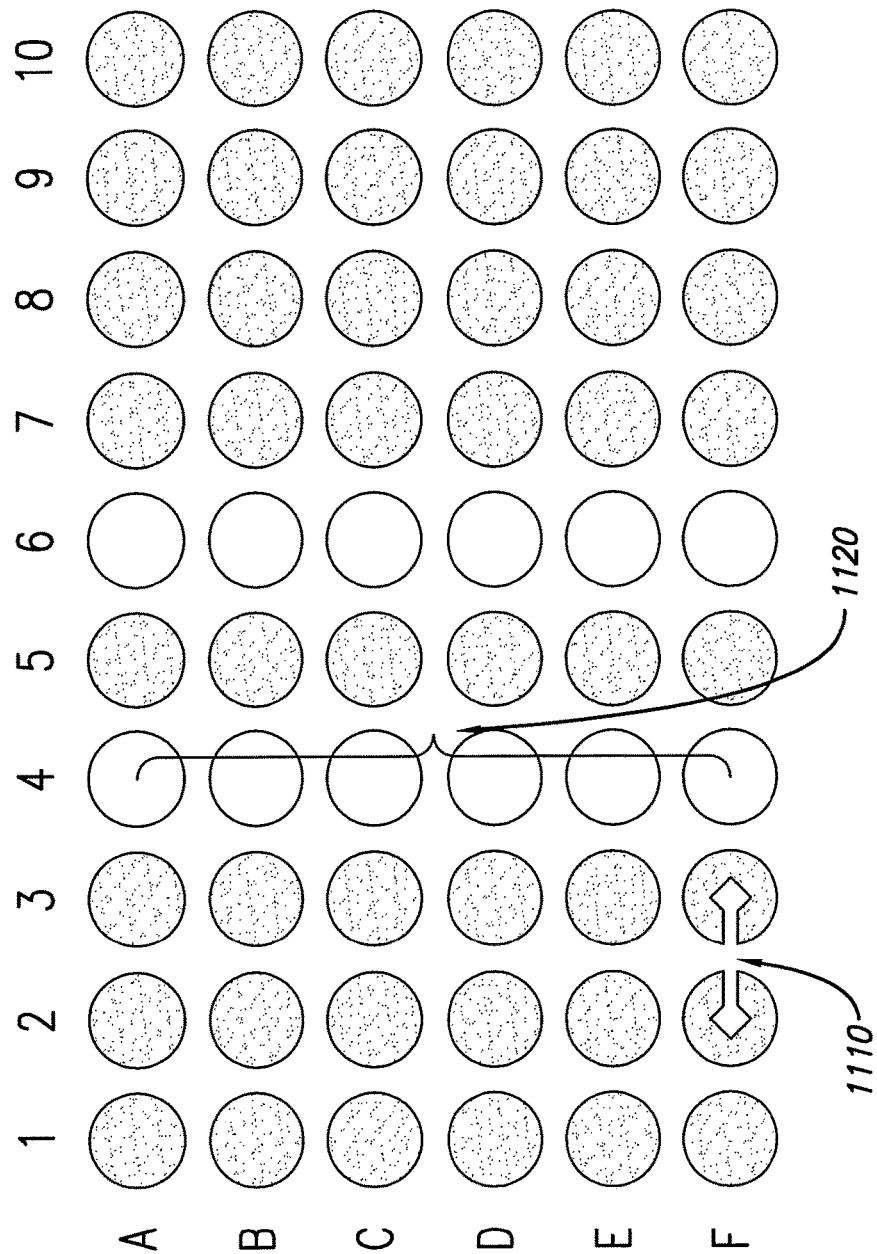
FIG. 11 shows electrode distance and pixel length for the retinal stimulation system with a 6×10 electrode array.

With reference to FIG. 11, the visual angle can be calculated by:

$$V = \frac{(l-1)*e}{r}$$

where l=pixel length 1120, e=distance between electrodes 1110, and r=distance per visual angle on the retina. The length of the projected image can then be converted to number of pixels by multiplying by the resolution scale of the touch screen monitor.

Prior to computing the STDA score, morphological processing can also be applied such that both the percept drawing and the projected stimulation pattern would have approximately the same relative line thickness. For the projected stimulation pattern, the morphological operation of thinning or shrinking can be applied before resizing to the projected scale. Decision of whether or not to use thinning or shrinking can be made based upon the shape properties such as its convex shape and Euler number. For the response pattern (percept drawing), the thinning operation is applied. After both the projected stimulation pattern and response pattern are processed through thinning so that the "noisy" pixels are removed, the dilation operation can be employed to increase the thickness of the lines and ensure both patterns would have about the same line thickness.

2. Pattern Matching and Finding Maximum STDA

The next important step is to match the stimulation pattern and the percept drawing to calculate the STDA score. The pattern matching and STDA scoring may comprise the following steps:

A. Find Maximum Window Size

Figure 12:
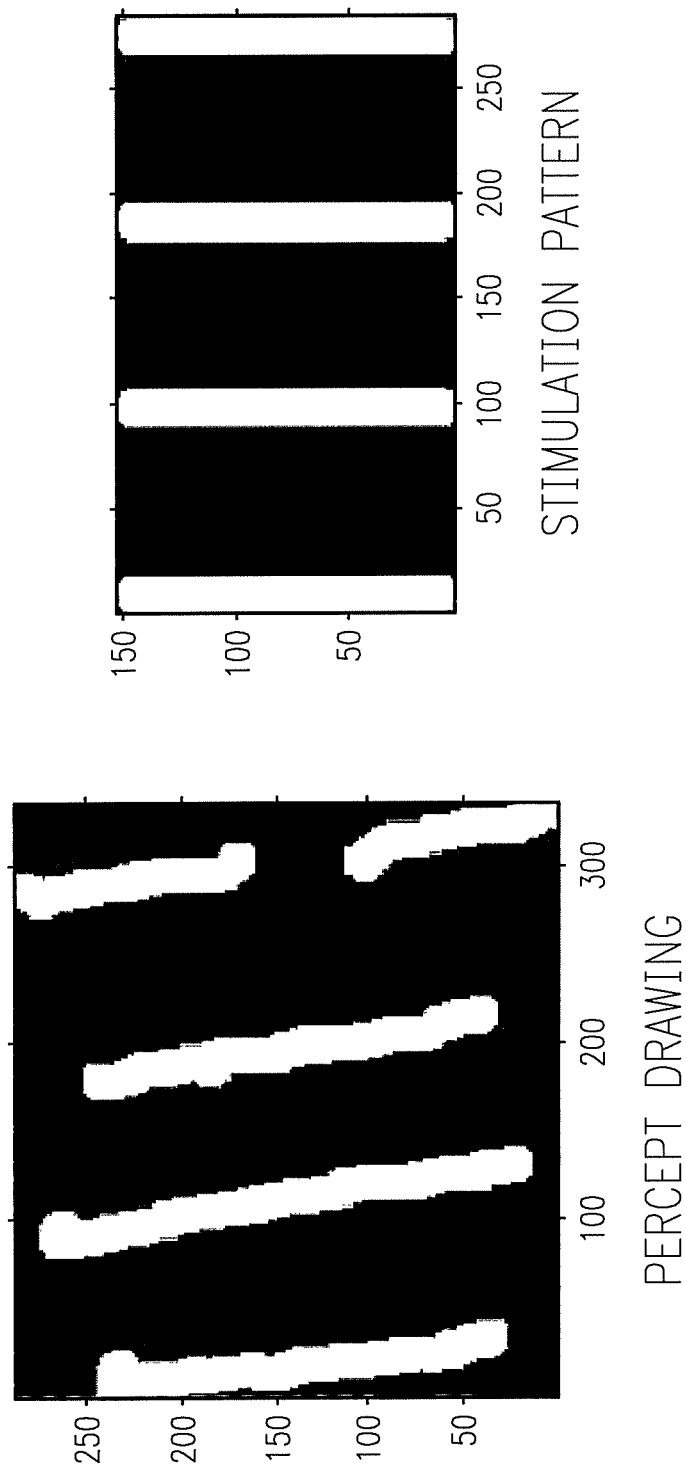
FIG. 12 shows an exemplary test sample with a maximum window size to match to the projected stimulation pattern.

After the image processing steps described above, the projected stimulation pattern can have a size around 200× 200 pixels. The first step is to find the maximum window size between the percept drawing and the projected stimulation pattern. In the example as illustrated in FIG. 12, the maximum window size is approximately 300×350 pixels.

B. Create a Reference for Comparison

Figure 13:
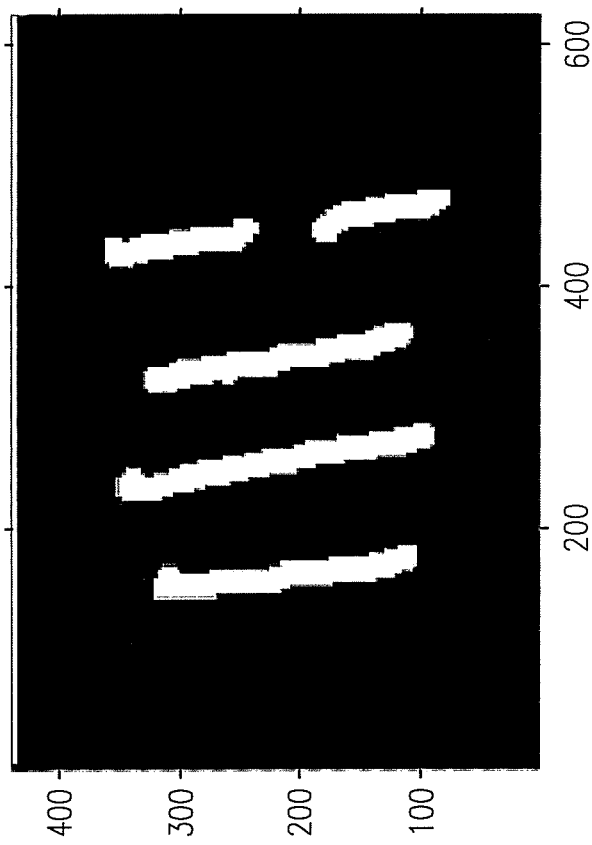
FIG. 13 shows placement of a larger pattern in the center of a window. Specifically.

The larger image, in pixel count, of the percept drawing and the projected stimulation pattern is placed in the center of a window as illustrated in FIG. 13. In this case the larger image is the percept drawing.

C. Adjust the Size of the Smaller Pattern

Figure 14:
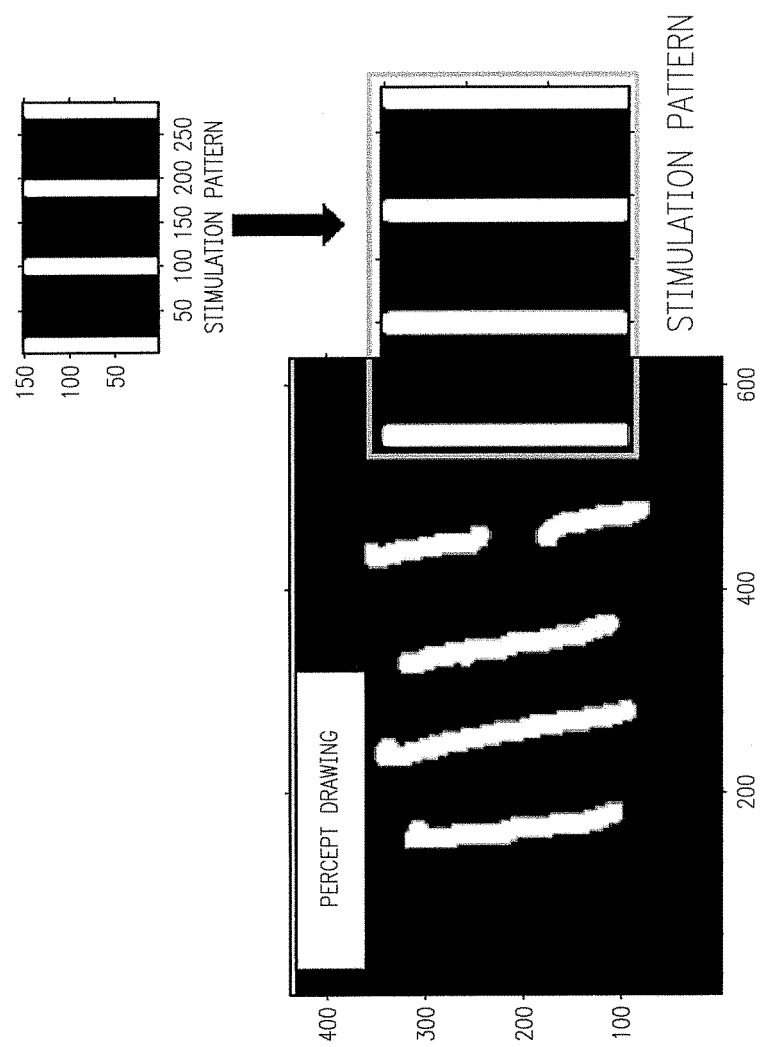
FIG. 14 shows upsizing of the stimulation pattern to be of a similar size as the percept drawing.

In this case as shown in FIG. 14, the stimulation pattern is upscaled by a scaling factor so that it would have a size comparable to the size of the larger pattern, which in this case, is the percept drawing.

Figure 15:
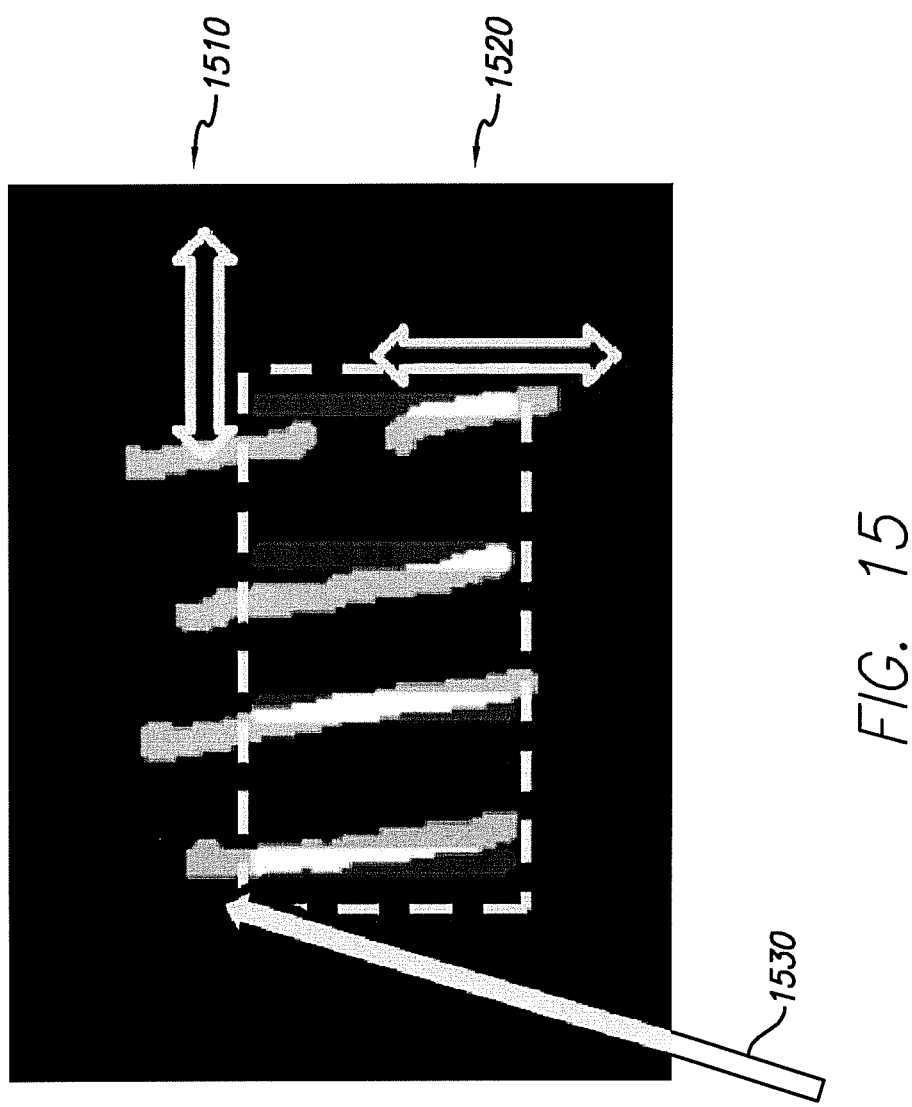
FIG. 15 shows an exemplary adjustment of the x-y location of the stimulation pattern by translation relative to the percept drawing to look for a maximum STDA score.

D. Pattern Alignment by Translation and Rotation to Calculate Maximum STDA Score As shown in FIG. 15, the stimulation pattern is shifted in the x-y plane by translation in the x-direction 1510 and y-direction 1520 relative to the centered percept drawing 1530. The STDA score is computed at each x-y translation step to find the translational pattern alignment between the stimulation pattern and the percept drawing which results in the maximum STDA score.

Many optimization methods exist for seeking a maximum in a space. For example, a coarse x-y step size can be used and minimum and maximum x-y locations where the STDA score becomes non-zero are recorded. The process can be then repeated within this window with a finer x-y step size to search for the maximum STDA score by translation in x-y.

After the maximum STDA score is found by translation in x-y, the STDA score is computed again by rotating one of the two patterns relative to the other in 1 degree increments from −10 deg to +10 deg. The maximum STDA score through rotation and translation in x-y can be used as the final STDA score.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. For example, the person skilled in the art will understand that the number steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Duda, Richard O., Peter E. Hart, and David G. Stork. *Pattern Classification.* New York: Wiley, 2001.
2. Domeniconi, C., Peng, J., Gunopulos, D.: Locally adaptive metric nearest-neighbor classification. IEEE Trans. Pattern Anal. Mach. Intell. 24(9), 1281-1285 (2002)
3. Kasturi, R. et al, 'Framework for Performance Evaluation of Face, Text, and Vehicle Detection and Tracking in Video: Data, Metrics, and Protocol', Pattern Analysis and Machine Intelligence, IEEE Transactions on, 2009, 31, (2)
4. "Visual Angle" Wikipedia, the Free Encyclopedia. 20 Jan. 2011. http://en.wikipedia.org/wiki/Visual_angle. URL verified 19 Apr. 2011.

The invention claimed is:

1. A method, comprising:
    providing a visual prosthesis a portion of which is adapted to be implanted in a subject, the visual prosthesis comprising a video processor and an array of electrodes;
    selecting and defining a first set of geometric shapes;
    selecting and defining a second set of geometric shapes;
    displaying a geometric shape from the first set of geometric shapes to the subject, wherein the displaying is by stimulating a plurality of electrodes in a multi-electrode pattern within the array of electrodes corresponding to the geometric shape;
    recording a drawing by the subject on an electronic input device of the geometric shape perceived by the subject, thus creating a described shape;
    comparing the described shape to geometric shapes from the second set of geometric shapes and determining a selected shape in the second set of geometric shapes closest to the described shape using an automatic tool; and
    adjusting the visual prosthesis based on the comparing of the described shape and the selected shape, thus performing spatial fitting for the visual prosthesis;
    wherein the steps of selecting, comparing, recording and adjusting are by autonomous processes in the video processor.

2. The method according to claim 1, wherein the stimulating of electrodes is by frequency encoding.

3. The method according to claim 1, wherein the stimulating of electrodes is by amplitude encoding.

4. A visual prosthesis, comprising:
a control device adapted for selecting and defining a first set of geometric shapes, a second set of geometric shapes and a third set of geometric shapes;
an array of electrodes configured for placement in proximity of a visual neural tissue of a subject;
a neural stimulator, coupled to the control device and the array of electrodes, adapted for applying stimuli to the visual neural tissue of the subject to elicit percepts and adapted for displaying a geometric shape from the first set of geometric shapes to the subject, wherein the displaying is by stimulating a plurality of electrodes in a multi-electrode pattern within the array of electrodes corresponding to the geometric shape; and
means for recording a drawing by the subject of the geometric shape perceived by the subject on an electronic input device, thus creating a described shape, wherein the control device is further adapted for:
comparing the described shape to geometric shapes from a second set of geometric shapes and selecting a selected shape from the second set of geometric shapes closest to the described shape, and
adjusting the selection of electrodes to be stimulated in the array of electrodes corresponding to a geometric shape from a third set of geometric shapes based on the comparing, thus improving spatial fitting for perceived image of the visual prosthesis.

5. The method according to claim 4 wherein the first set of geometric shapes and the second set of geometric shapes are the same.

* * * * *